United States Patent [19]
Neigut

[11] Patent Number: 6,048,886
[45] Date of Patent: Apr. 11, 2000

[54] COMPOSITIONS AND DELIVERY SYSTEMS FOR THE TOPICAL TREATMENT OF PSORIASIS AND OTHER CONDITIONS OF THE SKIN

[76] Inventor: Stanley Neigut, 10 Red Rowan La., Plymouth Meeting, Pa. 19462

[21] Appl. No.: 09/409,278

[22] Filed: Sep. 30, 1999

Related U.S. Application Data

[60] Provisional application No. 60/103,004, Oct. 5, 1998.

[51] Int. Cl.⁷ ..................................................... A61K 31/12
[52] U.S. Cl. .............................................................. 514/412
[58] Field of Search ............................................... 514/690

[56] References Cited

U.S. PATENT DOCUMENTS

| | | | |
|---|---|---|---|
| 4,654,373 | 3/1987 | Bertelli | 514/690 |
| 5,378,461 | 1/1995 | Neigut | 424/94.1 |
| 5,527,789 | 6/1996 | Nyce | 514/178 |

*Primary Examiner*—Raymond Henley, III
*Attorney, Agent, or Firm*—Whitham, Curtis & Whitham

[57] ABSTRACT

The invention provides compositions and methods for the application of those compositions in order to treat biological surfaces, especially the skin. The compositions contain a ubiquinone, may include other antioxidant agents (including melatonin), and may include an abrasive. The means of application may be by rubbing the composition into the skin, by means of a transdermal patch, or by rubbing the composition into the skin followed by application of a transdermal patch. The compositions and methods are useful for treating a variety of skin conditions, including psoriasis and hyper-pigmentation, and may also be used for cosmetic purposes and the prevention of skin damage.

24 Claims, No Drawings

COMPOSITIONS AND DELIVERY SYSTEMS FOR THE TOPICAL TREATMENT OF PSORIASIS AND OTHER CONDITIONS OF THE SKIN

CROSS-REFERENCE TO RELATED APPLICATIONS

This application is a continuation-in-part (CIP) of the provisional application Ser. No. 60/103,004 filed on Oct. 5, 1998, and the complete contents of that application are herein incorporated by reference.

DESCRIPTION

BACKGROUND OF THE INVENTION

1. Field of the Invention

The invention generally relates to the treatment of skin conditions such as psoriasis. In particular, the invention provides methods for treating skin, which is either damaged or undamaged, using compositions containing a ubiquinone and an abrasive, and for delivering compositions containing a ubiquinone by means of a transdermal patch.

2. Background of the Invention

The skin provides an essential protective barrier against environmental challenges such as radiation, extremes of temperature, excessive dryness, invasion by infectious organisms, and many others. As such, the maintenance of the health of the skin is of great importance for the overall preservation of well-being. This maintenance includes both preventative skin care and attention to rapid and effective healing of pathological skin conditions.

Much effort has been exerted in understanding the factors which promote healthy skin, especially those factors which are "naturally occurring", i.e. biological substances which are the components of the skin's endogenous protective and healing mechanisms. For example, it is known that the skin possesses an elaborate antioxidant defense system to deal with oxidative stress. Evidence for this is suggested by investigations of skin disorders such as Xeroderma pigmentosum, in which biopsies revealed an abnormally low level of activity of the enzyme catalase, which is involved in the defense against oxygen free radicals. Excessive exposure to environmental insults such as UV radiation can overwhelm the cutaneous antioxidant capacity, leading to oxidative damage and ultimately to skin cancer, immunosuppression, and premature skin aging.

Clinical studies of patients with active vitiligo have revealed diminished levels of several enzymatic and non-enzymatic antioxidants such as superoxide dismutase, catalase, glutathione peroxidase, vitamin E, glutathione reductase and polyunsaturated fatty acids in the epidermis. Since the levels of all these substances were depleted, it may reasonably be concluded that these antioxidants act in synergy and that their depletion manifests itself in the attendant skin disorders.

In the treatment of cutaneous wounds it has been observed that the levels of all enzymatic and non-enzymatic antioxidants except for glutathione reductase are severely decreased. In fact, none of these antioxidants except for glutathione were able to recover their normal levels as long as 14 days past wounding.

Hope for the successful treatment of such conditions lies in the identification of protective substances and in understanding their role in healing. One substance which has been implicated is the coenzyme, CoEnzyme Q, also known as ubiquinone, because it is ubiquitous in biological systems. CoEnzyme Q is a quinone derivative with a long isoprenoid tail. The number of 5-carbon isoprene units in the coenzyme is variable. The most common form in mammals contains 10 isoprene units (CoEnzyme $Q_{10}$, or $COQ_{10}$), but other forms contain up to 15 isoprene units ($COQ_{15}$). COQ is the coenzyme for at least three mitochondrial enzymes (Complexes I, II, and III) as well as enzymes in other parts of the cell. These mitochondrial enzymes, which function in the oxidative phosphorylation pathway, are essential for the production of ATP, the energy source upon which all cellular functions depend. The biosynthesis of COQ is known to be a multi-stage process requiring at least eight vitamins and several trace elements.

Through investigative research it has been determined that $COQ_{10}$ has beneficial therapeutic effects for many skin disorders due to its antioxidant or free radical quenching properties. Administration of $COQ_{10}$ not only greatly reduces antioxidant damage to tissue but also improves the immunocompetance of the cells. These properties can be significantly enhanced by administration in combination with other nonenzymatic and enzymatic antioxidants. Based on a limited number of clinical trials, it has been discovered that $COQ_{10}$ works most effectively in the presence of certain vitamins and amino adds. Specifically these are Vitamins A, $B_6$, C, D, and E, glutathione, carnitine, arginine, taurine, cysteine and methionine. Other ingredients which also significantly improve the therapeutic efficacy of $COQ_{10}$ are the enzymes superoxide dismutase (SOD) and catalase, alpha-lipoic/dihydrolipoic acid, and proanthocyanadins. The improved efficacy is believed to be the result of the synergistic effect of each of the components with respect to the healing process. Periodontal disease has also been treated relatively successfully with $COQ_{10}$.

Other research has shown that the combination of SOD and glutathione are effective in inhibiting erythema induced by UVB radiation. Further improvement was also noted by the addition of squalene which alleviated skin irritation by suppression of superoxide anion production. Again, the combination of ingredients appears to be more effective than any one alone.

Research has shown that carnitine also enhances the healing of the skin. The application of carnitine to treat refractory venous, mixed, or arterial ulcers resulted in nearly complete regression of trophic lesions in 79% of patients tested. The only apparent side effect was that some patients experienced transitory cutaneous hyperemia at the site of drug injection. From these studies, it was concluded that carnitine would be effective in the treatment of cutaneous ulcers.

Alpha-lipoic acid, which plays an essential role in mitochondrial dehydrogenase reactions, has recently gained considerable attention as an antioxidant. Alpha-lipoic acid and its reduced form, dihydrolipoic acid (DHLA), react with potentially damaging reactive oxygen species such as superoxide radicals, hydroxyl radicals, hypochlorous acid, peroxyl radicals and singlet oxygen. It also protects membranes by interacting with Vitamin C and glutathione. In turn, glutathione enhances the effect of Vitamin E by inhibiting its peroxidation and free radical development. Among several biologically and pharmacologically active sulphur compounds which have been investigated, only alpha-lipoic and dihydrolipoic acid were found to be effective in providing protection to plasmid DNA against singlet molecular oxygen. Since alpha-lipoic acid is both oil and water soluble, it is considered to be the "missing link" between Vitamin E and Vitamin C metabolism.

Topical application of Vitamin E has been shown to modulate the skin's antioxidant network and to diminish ultraviolet induced oxidative damage to the skin. Pretreatment with Vitamin E was shown to increase dermal superoxide dismutase activity, and to protect epidermal glutathione peroxidase and SOD from depletion after exposure to UV radiation. As a result of Vitamin E application, both glutathione reductase and ascorbate levels increased in the skin. In addition, Vitamin E treatment significantly reduced the formation of epidermal lipid hydroperoxides. These results demonstrate that topical application of Vitamin E protects cutaneous tissues against oxidative stress and suggest that the underlying mechanism of this effect involves the up-regulation of a network of enzymatic and nonenzymatic antioxidants.

Melatonin is a natural hormone which is synthesized by the body and exists in every cell. It is derived from serotonin, a neurotransmitter which in turn is converted from an amino acid by the pineal gland. Age adversely affects the ability to synthesize melatonin and this decline is believed to play a prominent role in the aging process.

Melatonin exhibits strong antioxidant properties, particularly with regard to peroxyl and hydroxyl radicals, and there is evidence that it is also a potent inhibitor of nitric oxide. Nitric oxide is believed to play an important role in the stimulation of free radical damage.

Melatonin is a small molecule which is highly diffusable and requires no binding sites or receptors to function. Melatonin has primarily been associated with brain function and has never been used topically to treat skin tissue.

Melatonin protects cells by stimulating glutathione peroxidase which converts reduced glutathione to its oxidized state, thus inhibiting the production of hydroxyl radicals. Melatonin has been used by itself and as adjuvant treatment for cancer, heart disease, stroke and Alzheimer's disease with some successes. It is contended that melatonin stimulates natural antioxidant levels, improves DNA repair and enhances the neuro-endocrine and immune systems. It appears that melatonin, like $COQ_{10}$, plays a role as a potent antioxidant and as an immuno stimulant.

There currently does not seem to be any anecdotal evidence of the specific effect melatonin might have on the efficacy of topical skin treatment. However, since melatonin and $COQ_{10}$ are both ubiquitous and possess similar properties, it would seem that melatonin, with the advantage of its smaller molecular structure, could be an effective topical agent, either by itself or in synergistic combination with $COQ_{10}$ and/or other antioxidants. In Example 12 below, we show that this is indeed the case.

Even though progress has been made with respect to understanding the role of various naturally occurring substances in the healing and health maintenance of skin, especially with respect to the antioxidant properties of those substances, there is still a need for continued investigation. A number of conditions remain refractory to current treatment protocols, such as the highly problematic skin disease psoriasis. There is currently no effective treatment for psoriasis, and such a treatment would be highly beneficial to those who suffer from the condition. Many other skin conditions exist which currently have no really effective means of treatment, including keratosis, rosacea, and the scarring that results from acne vulgaris. For some of these conditions, little or no improvement occurs as a result of current treatment practices.

It would thus be of great benefit to those who suffer from pathological or disfiguring skin conditions of many types to have available improved preparations of substances which could ameliorate those conditions. In addition, it would be of great benefit to have available improved preparations of substances which could be used prophylactically in order to prevent the occurrence of skin damage due to environmental insult and oxidative stress.

Regardless of how many salutary ingredients a pharmaceutical preparation contains, in order to derive maximal benefit from it, the preparation must be administered in an efficacious manner. It would be of benefit to have available more efficient systems for the topical delivery of preparations intended to treat skin disorders.

SUMMARY OF THE INVENTION

It is an object of this invention to provide effective delivery methods and compositions for the treatment of biological surfaces. In a preferred embodiment, the biological surface is skin.

According to a first embodiment of the invention, a composition which includes a ubiquinone and an abrasive is applied. In a further embodiment of the present invention, the composition may include antioxidants and other agents. In a further embodiment of the present invention, the composition may include melatonin.

According to a second embodiment of the invention, a composition which includes a ubiquinone and may or may not include an abrasive is applied by means of a transdermal patch. In a further embodiment, the composition which is delivered via a transdermal patch may include antioxidants and other agents. In a further embodiment, application via a transdermal patch is preceded by treating the biological surface with an abrasive.

DETAILED DESCRIPTION OF THE PREFERRED EMBODIMENTS OF THE INVENTION

The present invention provides methods for the treatment of damaged or undamaged skin. In a first embodiment, the method includes applying to the skin a composition which contains a ubiquinone and an abrasive. In a second embodiment, the method includes applying to the skin a composition which contains a ubiquinone via the use of a transdermal patch. In another embodiment, the method includes two steps: first, a composition which contains a ubiquinone and an abrasive is applied to the skin; secondly, a composition which contains a ubiquinone is applied to the skin via the use of a transdermal patch.

The present invention provides improved delivery methods and compositions which are highly effective in the treatment of various pathological, cosmetic and disfiguring conditions of the skin. The compositions may be used for the treatment of conditions which have already manifested, or for the prevention of skin damage which might eventually lead to such a condition. Such pathological skin conditions include but are not limited to: psoriasis; keratosis (including actinic, solar and sebhorratic); rosacea; discrete and mottled hyper-pigmentation; dermatitis (including contact, atopic, subhorraic, senile, and scratch); herpes (both labialis and zoster); acne vulgaris scarring; photo damage; eczema; fine wrinkling; keloid and hypertrophic scar tissue; dryness; loss of skin elasticity; loss of skin clarity.

In a preferred embodiment of the present invention, the compositions of the instant invention are utilized to treat skin disorders. However, they may also be used to treat disorders of the membranes of orifices such as the eyes, ears, nose, mouth, umbilicus, urethra, anus, vagina, rectum and the like (all of which are more generally referred to as "biological surfaces"). The compositions of the instant invention may also be used to treat any biological surface which would benefit from the application of such preparations.

The compositions of the instant invention are comprised of a mixture several substances which are antioxidants. Specific formulations are given in the examples section below. Although treatment with a single or a few combined components of the antioxidant system have been relatively successful for treatment of a variety of conditions (as described in the Background section) the most promising results have been obtained when several antioxidant compounds were combined. The combination of antioxidant components appears to result in synergism of the therapeutic and protective effects. The compositions of the present invention thus comprise a mixture of components with demonstrated antioxidant activity. The components of the compositions of the present invention include but are not limited to various non-enzymatic antioxidants such as vitamins (for example, vitamins A, $B_6$, C, D, E, etc.), ubiquinones ($COQ_{10}$–$COQ_{15}$), glutathione, alpha-lipoic acid/DHLA, amino acids, proanthocyanadins, and various enzyme antioxidants such as glutathione peroxidase, catalase and superoxide dismutase. The compositions of the present invention may also include such agents as melatonin, which may be present at weight percentages ranging from 0.1 to 99%.

The preparation may also include an appropriate carrier, many of which are known to those of skill in the art. Examples of suitable carriers include but are not limited to; squalene, olive oil, corn oil, canola oil, peanut oil, safflower oil, flax oil, sunflower oil, mineral oil and castor, as well as such water-based carriers as glycerin, water, alcohol, propylene glycol and the like.

Clinical evaluations have demonstrated the efficacy of $COQ_{10}$ treatment for other conditions besides those relating to skin, including treatment of the eyes, nose, rectum, and vagina. Therefore, it is contemplated that all biological surfaces could benefit from application of the compositions thereto.

The compositions can take any suitable form including but not limited to sprays, gels, ointments, suspensions, emulsions, creams, powders or suppositories and the like.

In a preferred embodiment of the present invention, the compositions of this invention have been formulated to include an abrasive substance. As will be illustrated in the examples below, it has been found that the inclusion of an abrasive substance in the formulations of the present invention surprisingly and significantly enhances their effectiveness. It is likely that the abrasive promotes removal of dead or damaged intervening tissue and makes the underlying tissue more accessible to the therapeutic action of the compositions, as compared to analogous compositions which do not include an abrasive. Those of skill in the art will recognize that many appropriate abrasive substances are known and may be used in the practice of the instant invention. Examples include, but are not limited to, ground fruit pits, ground nut kernels, ground nut shells, grain hulls (from for example wheat, bran, oats, rice, etc.), saw dust, aluminum oxide, silica sand, pumice, plastic and acrylic grit, plastic flour, and ground corn cobs.

The present invention also contemplates a method of delivery for the compositions. Firstly, the preparation may include an abrasive as described above and be applied manually by massaging into the skin. However, as will be revealed in the examples below, it has been discovered that manual application followed by application of a "patch" which has been impregnated with the composition (less the abrasive), gives superior results compared to topical application alone. The composition used on the patch can be formulated with or without abrasives, however, formulations without abrasives may work best on the transdermal patch for promoting adhesion and increasing the quantity of active ingredients per square centimeter. Therefore, in a preferred embodiment of the present invention, the method of delivery of a composition is comprised of two steps:

1) topical administration of the composition which contains an abrasive, followed by
2) application of a "patch" containing the composition (with or without an abrasive), in order to sustain continued exposure to the composition.

Those of skill in the art will recognize that many types of patches exist which are suitable for use in the practice of the present invention. Any suitable patch which serves to appropriately deliver the compounds of the present invention may be used in the practice of the present invention. The chief requirements of the patch are that it adheres to the skin being treated, and that it delivers the ubiquinone and supporting chemical constituents to the skin. Delayed release mechanisms may be employed to assure long term delivery.

The exact protocol to be followed when utilizing the composition and delivery system of the present invention will vary from case to case and will depend on several factors, including the nature of the pathology being treated, the condition of the patient, etc. For example, it is anticipated that the formulation would be administered between 1 and 10 times daily, and more preferably 2 to 4 times per day.

The results of the case studies presented in Examples 7–9 below demonstrate that for certain conditions the topical treatment of the skin with compounds containing $COQ_{10}$, other antioxidants, and abrasives in a suitable carrier are therapeutically more effective that those which do not contain an abrasive. Any of the compounds as described in the Examples of the present invention may optionally include an abrasive. Study results also clearly reveal that transdermal delivery of $COQ_{10}$ and/or other antioxidants is more efficacious than other techniques of topical application.

For several types of skin conditions, therapeutic results can be optimized by the use of both an abrasive compound incorporating $COQ_{10}$ and transdermal delivery of other compounds incorporating $COQ_{10}$ as described in the Examples below. The choice of constituents, as well as their final concentration in the composition, can vary widely within the practice of this invention. The chief requirements of this invention is that the ubiquinone (which can be present at a weight percentage ranging from 0.01 to 99%) is either combined with an abrasive or is delivered transdermally. In the practice of the abrasive containing embodiment of this invention, the abrasive can be present at weight percentages ranging from 1–99%.

The following examples will serve to further illustrate compositions and methods of delivery of the compositions within the present invention. The Examples are meant to serve as illustrations and should not be construed so as to limit the scope of the instant invention in any way.

EXAMPLES

Methods

EXAMPLE 1

Composition and Method of Manufacture of Compound I

| CONSTITUENTS | % WEIGHT |
|---|---|
| Carrier | 56.0 |
| Vitamin E | 10.9 |
| Vitamin A | 0.8 |
| Vitamin D | 0.1 |
| Gamma Linolenic Acid (GLA) | 4.5 |
| Lecithin | 4.5 |
| $COQ_{10-15}$ | 1.3 |
| l Alcohol | 2.9 |
| Purified Water | 4.4 |
| Abrasive | 14.6 |

Method of Manufacture

Oil Phase

Heat carrier to 120° F. and mix in $COQ_{10}$ until fully dissolved, then add lecithin, GLA, Vitamin E, Vitamin A and Vitamin D in that order. Add appropriate thickener and blend at high speed. Cool to 95° F.

Water Phase

Mix water and alcohol and heat to 95° F., add surfactants and blend at high speed.

Final Mixing

Add water phase to oil phase and blend at high speed for approximately 5 minutes. Cool to 70° F. Add abrasive compound and blend until thoroughly mixed.

EXAMPLE 2

Compositions and Method of Manufacture of Compound II

| CONSTITUENTS | % WEIGHT |
|---|---|
| Carrier | 63.6 |
| Vitamin E | 10.2 |
| Vitamin A | 0.8 |
| Vitamin D | 0.2 |
| Vitamin $B_6$ | 0.6 |
| Ascorbyl Palmitate | 0.6 |
| Selenium | 0.01 |
| Alpha Lipoic Acid/DHLA | 0.6 |
| Glutathione | 0.6 |
| Proanthocyanadin | 0.3 |
| Superoxide Dismutase | 0.3 |
| GLA | 4.0 |
| Lecithin | 6.4 |
| $COQ_{10-15}$ | 1.6 |
| Alcohol | 2.5 |
| Purified Water | 7.6 |

Method of Manufacture

Oil Phase

Heat carrier to 120° F. and add $COQ_{10}$, Ascorbyl Palmitate, and Alpha Lipoic Acid. Mix until completely dissolved. To this mixture add Lecithin, GLA and Vitamins E, A and D in that order. Add appropriate thickener and blend thoroughly at high speed. Cool to 95° F.

Water Phase

Mix water and alcohol and heat to 125° F. Add Superoxide Dismutase, Selenium, Glutathione, Proanthocyanadin and blend at high speed. Cool to 95° F. and add Vitamin $B_6$ and surfactants. Blend at high speed.

Final Mixing

Add water phase to oil phase and blend at high shear speed.

| CONSTITUENT | % WEIGHT |
|---|---|
| Carrier | 62.6 |
| Vitamin E | 4.9 |
| Vitamin A | 1.0 |
| Vitamin D | 0.1 |
| Vitamin $B_6$ | 0.6 |
| Vitamin C | 0.6 |
| Lecithin | 5.3 |
| GLA | 3.7 |
| $COQ_{10-15}$ | 1.6 |
| Alpha Lipoic Acid/DHLA | 0.6 |
| Selenium | 0.01 |
| Glutathione | 0.6 |
| Carnetine | 0.6 |
| Arginine | 0.6 |
| Taurine | 0.6 |
| Cysteine | 0.6 |
| Methionine | 0.6 |
| Dimethylglycine | 0.3 |
| Superoxide Dismutase | 0.3 |
| Proanthrocyanadin | 0.3 |
| Alcohol | 3.1 |
| Purified Water | 6.3 |

The method of manufacture or Compound III is similar to that described in Example 2 for Compound II. Oil soluble materials and thickeners are blended with the carrier at 120° F. and allowed to cool to 95° F. Water soluble materials are blended with water, alcohol and surfactants at 125° F. and allowed to cool to 95° F. Oil phase and water phase are then blended at high shear speed.

EXAMPLE 4

Composition and Method of Manufacture of Compound IV

| CONSTITUENT | % of WEIGHT |
|---|---|
| Carrier | 62.4 |
| Vitamin E | 10.0 |
| Vitamin A | 0.8 |
| Vitamin D | 0.15 |
| Vitamin C | 0.9 |
| Vitamin $B_6$ | 0.9 |
| Alpha Lipoic Acid/DHLA | 0.9 |
| $COQ_{10-15}$ | 1.6 |
| Glutathione | 0.9 |
| Proanthrocyanadins | 0.5 |
| Selenium | 0.01 |
| Lecithin | 6.3 |
| GLA | 4.1 |
| Superoxide Dismutase | 0.5 |
| Zinc Gluconate/Oxide | 0.6 |
| Purified Water | 6.3 |
| Alcohol | 3.1 |

Method of Manufacture

The Method of Manufacture of Compound IV is similar to that of Compound III in Example 3. Oil soluble materials and thickeners are blended with the carrier at 120° F. and allowed to cool to 95° F. Water soluble materials are blended with water, alcohol and surfactants at 125° F. and allowed to cool to 95° F. Oil phase and water phase are blended at high shear speed.

EXAMPLE 5

Composition and Method of Manufacture of Compound V

| CONSTITUENT | % WEIGHT |
| --- | --- |
| Carrier | 65.5 |
| Vitamin | 12.8 |
| Vitamin A | 0.9 |
| Vitamin D | 0.1 |
| GLA | 5.3 |
| Lecithin | 5.3 |
| $COQ_{10-15}$ | 1.5 |
| Vitamin K | 0.1 |
| Purified Water | 5.1 |
| Alcohol | 3.4 |

Method of Manufacture

Oil Phase

Heat carrier to 120° F. and mix in $COQ_{10}$ until fully dissolved then add lecithin, Vitamin K, GLA, Vitamin E, Vitamin A and Vitamin D, in that order. Add appropriate thickener and blend at high speed. Cool to 95° F.

Water Phase

Mix water and alcohol and heat to 95° F., add surfactants and blend at high speed.

Final Mixing

Add water phase to oil phase and blend at high speed for approximately 5 minutes. Allow to cool

EXAMPLE 6

Composition and Method of Manufacture of Compound VI

| CONSTITUENT | % WEIGHT |
| --- | --- |
| Carrier | 70.8 |
| Vitamin E | 14.0 |
| Vitamin A | 0.9 |
| Vitamin D | 0.1 |
| GLA | 5.8 |
| Lecithin | 5.8 |
| $COQ_{10-15}$ | 1.7 |
| Melatonin | 1.0 |

Method of Manufacture

Heat carrier to 120° F. and mix in $COQ_{10}$ until fully dissolved, then add lecithin, Melatonin (water soluble), GLA, Vitamin E, Vitamin A and Vitamin D in that order.

If desired, the formulation can be produced as an ointment or emulsion by adding mitable emulsifiers, thickeners and surfactants during the manufacturing process.

EXAMPLE 7

Composition and Method of Manufacture of Compound VI

| Constituents | % Weight |
| --- | --- |
| carrier | 55.0 |
| Vitamin E | 10.9 |
| Vitamin A | 0.8 |
| Vitamin D | 0.1 |
| GLA | 4.5 |
| Lecithin | 4.5 |
| $COQ_{10-15}$ | 1.3 |
| Melatonin | 1.0 |
| Alcohol | 2.9 |
| Purified Water | 4.4 |
| Abrasive | 14.6 |

Method of Manufacture

Oil Phase

Heat carrier to 120° F. and mix in $COQ_{10}$ until fully dissolved, then add GLA, Vitamin E, Vitamin A and Vitamin D, in that order. Add appropriate thickener and blend at high speed. Cool to 95° F.

Water Phase

Mix water and alcohol and heat to 95° F. Add melatonin and dissolve thoroughly. Add surfactants and blend at high speed.

Final Mixing

Add water phase and blend at high speed for approximately 5 minutes. Cool to 70° F. Add abrasive compound and blend until thoroughly mixed.

Note: This compound may be produced without an abrasive and weights adjusted accordingly.

EXAMPLE 8

Case Study 1: Treatment of Psoriasis with Compounds I and IV

Eight patients were selected, each with moderate to severs psoriasis. Affected areas were bilateral, occurring on both elbows, knees, forearms and/or thighs. The patients were treated on the elbows and knees as follows:

The left elbow and right knee of each patient were treated twice daily with Compound IV alone. In contrast, the right elbow and left knee were treated once daily in two stages. The first was a single application of Compound I which, after being massaged in, was removed from the skin surface. This was followed by the application of a transdermal patch impregnated with Compound IV. The thighs and forearms were untreated and acted as controls. The results were dramatic.

Application of either Compound I or IV on affected areas drew almost immediate relief from severe itching. Compound I, due to its abrasive effect, caused slight irritation to surrounding tissue at first. This subsided within a few days. Within five days there was a marked reduction in scale and erythema for all areas treated. However, the areas treated with both Compounds I and IV showed a greater reduction of inflammation and thinner plaque than those areas treated with Compound IV alone. Ten days after beginning treatment the areas treated with Compounds I and IV were completely free of scale and inflamation. The skin had normal elasticity and color. A similar result was observed in those patients treated with Compound IV alone but this was not achieved until sixteen days after beginning treatment. The untreated control areas remained the same or became a little worse than at the beginning of the study. Thus it can be concluded that Compound IV is effective in treating psoriasis but that using Compounds I and IV delivered in sequence accelerated the healing process by 33%.

EXAMPLE 9

Case Study 2: Treatment of Rosacea with Compound II

Six patients with moderate to severe Rosacea on their faces were treated as follows.

Group 1. Three patients were treated on their foreheads and cheeks with Compound II. Compound II was applied and massaged into the skin three times daily.

Group 2. The remaining three patients were treated in approximately the same locations but with a variation in procedure. First, only two applications were made daily. The first of the two applications was made in the manner identical to that of Group 1. But the second application was delivered by a transdermal patch at bed time and allowed to remain on the sites until morning.

Substantial differences in results between Group 1 and Group 2 could be seen in a relatively short period of time. Within three days the erythema associated with Rosacea on the patients using the transdermal patch were significantly lighter in color than those not using the transdermal patch. In those cases where edema had been observed, this condition had also shown significant improvement. Within two weeks the areas treated with the transdermal patch appeared to be normal in color, elasticity and smoothness. The patients not treated with the transdermal patch showed improvement but there was some residual erythema and a nominal degree of edema. Areas which were used as controls had not been treated in any manner and their conditions remained the same or somewhat worse as compared to the beginning of the study.

The noses of one group of the above patients were treated with Compound II. Applications of Compound II were made three times daily by massaging into the skin. A second group had only two applications daily. The first application was made in a manner identical to that of the first group. However, the second application was made with a transdermal patch which remained on the nose overnight. The results of this study substantiated the results of the previous study in that the use of the transdermal patch greatly accelerated the healing process even though the same therapeutic compound (Compound II) was used. In the case of treating Rosacea on the nose, the transdermal patch accelerated the healing process time by at least 35% and the difference in the appearance of the skin treated by the two different procedures was immediately apparent. We conclude that use of the transdermal patch for the application of these compounds to the skin markedly improves the efficacy of treatment.

EXAMPLE 10

Case Study 3: Treatment of Photo Damage with Compounds I and II

Ten Caucasian male patients, ages ranging from 56 to 78, and each having severe photo damage to the backs of both hands were selected for this study. The skin damage comprised variable pigmented solar and sebhorratic keratotic lesions, and additional mottled pigmentation. Males were selected because their skin is somewhat thicker than females. It should be noted that dermatologists consider hands to be one of the most difficult areas of the human body to treat.

The right hands of five patients were treated in two stages. The first application used Compound I which contains an abrasive. This was massaged into the skin for approximately one minute and the excess residue was then removed. Compound VII was then applied. A second application of Compound VII was made at bedtime using a transdermal patch and was allowed to remain on site until morning. This same procedure was followed every day.

The left hands of the patients were treated three times per day using the same procedure as above, but they did not receive an overnight transdermal patch. Within three weeks many of the hyper-pigmented lesions of both hands showed significant improvement. Examination of the hands during the eighth week revealed further improvement in both hands but the mottled pigmentation of the hands treated with the transdermal patch were considerably lighter than those of the hands not treated with the transdermal patch. During week 12, the pigmentation (both discrete and mottled) on the hands treated with the transdermal patch was approximately 25% lighter than the hands not treated with a transdermal patch.

Five patients in a remaining group were treated in a different manner. The right hands of these patients were treated three times daily with Compound VII. The left hands were also treated with Compound VII but only twice daily. The second application on the left hands was made at night and delivered with a transdermal patch which remained on the skin all night.

Examination of both hands after six weeks showed a distinctly lighter color of hyper-pigmented areas on the left hands which had been treated with the transdermal patch, compared to the right hands. Examination of both hands after 12 weeks substantiated the results of previous studies, i.e. that the areas treated with a transdermal patch clearly showed accelerated and more pronounced improvements of the condition than the areas not treated with a transdermal patch. Thus, for this particular condition, results were optimized by the use of both abrasive compound and transdermal delivery.

EXAMPLE 11

Case Study IV, Treatment of Atopic Dermatitis with Compounds VI and VII

Eight Caucasian patients ranging in age from 28 to 52, diagnosed with atopic dermatitis, were divided into two subgroups of four each. Group A patients manifested sub-acute scaly rough red lesions on the face, neck and upper torso. There was also moderate epidermal inflammation. Group B symptoms were chronic dry lichenfied raised lesions on the hands, knees, neck and upper torso. Several of those lesions were hyper-pigmented and definitively demarcated. Both groups A and B exhibited moderate to severe itching. Those patients with very severe itching had been prescribed antipuretics and were uncomfortable because of the side effects.

Because of the hyper-irritability of the skin of some patients with atopic dermatitis, it was considered prudent to avoid abrasive compounds in the treatment of Group A patients. Consequently, Group A was treated with Compound VI only.

Two areas of the face and neck were selected for treatment three times daily by massaging Compound VI into those areas. Two other areas on the face and neck were treated twice per day with Compound VI using the same procedure as above. However, the second application was delivered by a transdermal patch which remained on site overnight. Areas on the torso were not treated.

All patients exhibited virtually immediate relief from itching. Within three days the scaly patches were gone from all patients. In seven days all patients had shown significant improvement. However, the skin color of those areas treated with the transdermal patch appeared normal while those areas not treated with a transdermal patch exhibited some degree of erythema. No change was observed on untreated areas of the torso.

Group B. Because of their elevated, thick, hyperpigmented lesions, patients in this group were treated in a manner somewhat similar to those suffering from psoriasis. It was believed that the use of an abrasive compound would prove efficacious in the treatment of patients with these symptoms.

The knees of two patients were treated once per day with compound VII which contained an abrasive. This compound was massaged into the skin for approximately one to one and a half minutes. The residue was then removed and an application of Compound VI was immediately massaged into the skin. The second application of Compound VI was made at bedtime.

The knees of the two remaining patients were treated three times per day only with Compound VI. No abrasive compound was used. Untreated areas of the neck and upper torso served as controls.

Within one week the lesions of all patients had thinned considerably. The lesions which were treated with the abrasive compound, however, were thinner than those not treated with the abrasive compound and the pigmentation was lighter. Within two weeks the skin treated with the abrasive compound was normal, exhibiting very little pigmentation and good skin elasticity. At this time it was decided to eliminate use of the abrasive compound and continue to treat only with Compound VI. The areas not treated with the abrasive compound were demonstrably improved but still retained approximately 25% more pigmentation than those areas which were treated with the abrasive compound and skin elasticity was also less.

As in the other Examples presented previously, this Example demonstrates that the use of an abrasive compound containing ubiquinone for certain types of skin conditions is more effective than using a non-abrasive compound. Using the abrasive compound not only shortens the time of the healing process but also enables one to reduce the frequency of daily application.

It has also been demonstrated that the application of a transdermal patch containing a ubiquinone is more efficacious with regard to the acceleration of the healing process and reduction of application frequency than not using a transdermal patch.

For those conditions which can be treated with both an abrasive compound and a transdermal patch, this synergy optimizes therapeutic results both in respect to shortening healing time and the quality of the result.

EXAMPLE 12

Case Study 5-Comparative Treatment of Seborrheic Dermatitis with COQ and Melatonin This study was conducted to determine the relative effectiveness of two agents for topical application, i.e. $COQ_{10}$ and melatonin, for this type of skin condition.

Four patients with moderate seborrheic dermatitis on the face, scalp and chest were selected. The affected areas exhibited generalized moderate erythema and light scale. The scalps had some scaly encrustations and there was profuse dandruff on the scalp and hair.

Two patients were treated with a 2% suspension of melatonin in squalane. The patients were instructed to massage this product into the scalp once per day during the evening and allow it to stay overnight. The same suspension was to be massaged into the other affected areas three times per day. The patients were also instructed to wash their scalps every morning with a medium Ph non-medicated shampoo. The melatonin suspension was subsequently applied to a slightly damp scalp. This procedure was repeated for seven days.

The remaining two patients followed the same instructions as above but a 2% solution of $COQ_{10}$ in squalane was used instead of melatonin.

Examination of all patients after four days revealed that scalp encrustations were no longer physically present. There was, however, some degree of erythema. Areas of the face which had been treated showed similar results. By the end of the week the scalps of all patients were completely clear of scale and dandruff but there was some degree of erythema. The faces were also clear of scale but some degree of erythema also remained. The chest had not been treated and was used as control. No changes had been observed in untreated areas.

It was then decided to combine the $COQ_{10}$ and Melatonin in equal proportions, i.e. 2% each in squalane.

The chest areas which were untreated as controls were now used as sites for the application of the $COQ_{10}$ and melatonin combination. The skin areas were characterized by light to moderate red scaly patches and light to moderate erythema. There was also mild to moderate itching.

Patients were instructed to apply and massage the mixture into affected areas three times per day. They were instructed to wash affected areas during the evening with a non-medicated soap impregnated into a sponge or wash cloth. This provided a very mild abrasion to remove scale.

The itching of all patients was virtually eliminated almost immediately after the first application.

Patients were examined four days after initial treatment. All scale had been removed and there was a marked reduction of erythema. By the end of the week the treated areas remained scale free. There was no sign of erythema. Skin color was normal and elastic.

For this particular skin condition it appears that $COQ_{10}$ and melatonin used independently appear to be equally effective. However, the combination of $COQ_{10}$ and melatonin seem to be synergistic, resulting in more efficacious treatment of erythema associated with this skin condition. Since there are a number of skin disorders with similar symptoms, it can be concluded that melatonin, particularly in combination with $COQ_{10}$, can be an effective topical therapeutic agent.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A method for preventing or treating skin disorders, comprising:

applying a composition including a ubiquinone and an abrasive to skin, said abrasive being present in an amount ranging from 1–99 weight % and said ubiquinone being present in an amount ranging from 0.01 to 99 weight %.

2. The method of claim 1 wherein said applying is performed by rubbing said composition against said skin.

3. The method of claim 1 wherein said composition includes an antioxidant.

4. The method of claim 1 wherein said composition includes melatonin, said melatonin being present in an amount ranging from 0.1 to 99 weight %.

5. The method of claim 1 further comprising the step of applying a patch containing a ubiquinone to said skin.

6. A method for preventing or treating skin disorders, comprising:

positioning a patch on skin, said patch including a ubiquinone which can be delivered therefrom to said skin.

7. The method of claim 6 further comprising the step of treating said skin with an abrasive prior to said positioning step.

8. The method of claim 7 wherein said abrasive is used in combination with a ubiquinone.

9. The method of claim 6 wherein said patch further includes an antioxidant.

10. The method of claim 6 wherein said patch further includes melatonin, said melatonin being present in an amount ranging from 0.1 to 99 weight %.

11. The method of claim 1 wherein said skin disorder is selected from the group consisting of:

psoriasis, rosacea, photodamaged skin, atopic dermatitis and seborrheic dermatitis.

12. The method of claim 11 wherein said skin disorder is psoriasis.

13. The method of claim 11 wherein said skin disorder is rosacea.

14. The method of claim 11 wherein said skin disorder is photodamaged skin.

15. The method of claim 11 wherein said skin disorder is atopic dermatitis.

16. The method of claim 11 wherein said skin disorder is seborrheic dermatitis.

17. The method of claim 6 wherein said skin disorder is selected from the group consisting of:

psoriasis, rosacea, photodamaged skin, atopic dermatitis and seborrheic dermatitis.

18. The method of claim 17 wherein said skin disorder is psoriasis.

19. The method of claim 17 wherein said skin disorder is rosacea.

20. The method of claim 17 wherein said skin disorder is photodamaged skin.

21. The method of claim 17 wherein said skin disorder is atopic dermatitis.

22. The method of claim 17 wherein said skin disorder is seborrheic dermatitis.

23. The method of claim 1 wherein said composition includes amino acids.

24. The method of claim 6 wherein said composition includes amino acids.

* * * * *

UNITED STATES PATENT AND TRADEMARK OFFICE
CERTIFICATE OF CORRECTION

PATENT NO. : 6,048,886
DATED : April 11, 2000
INVENTOR(S) : Neigut

It is certified that error appears in the above-identified patent and that said Letters Patent are hereby corrected as shown below:

In the Specification, at column 5, line 8, after "mixture" insert "of".

In the Specification, at column 6, line 42, replace "that" with "than".

In the Examples, at column 7, line 18, in front of "alcohol" delete "1".

In the Examples, at column 8, line 9, insert:
"EXAMPLE 3. Composition and Method of Manufacture of Compound III."

Signed and Sealed this

Twenty-fourth Day of April, 2001

NICHOLAS P. GODICI

Attest:

Attesting Officer

Acting Director of the United States Patent and Trademark Office